US011464797B2

(12) United States Patent
Zhou

(10) Patent No.: US 11,464,797 B2
(45) Date of Patent: Oct. 11, 2022

(54) USE OF VITAMIN COMPOSITION IN PREPARING DRUG FOR PREVENTING, TREATING, OR DELAYING ALZHEIMER'S DISEASE

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

(21) Appl. No.: 16/491,560

(22) PCT Filed: Feb. 24, 2018

(86) PCT No.: PCT/CN2018/077107
§ 371 (c)(1),
(2) Date: Sep. 5, 2019

(87) PCT Pub. No.: WO2018/161808
PCT Pub. Date: Sep. 13, 2018

(65) Prior Publication Data
US 2020/0030358 A1    Jan. 30, 2020

(30) Foreign Application Priority Data
Mar. 7, 2017   (CN) .......................... 201710131111.X

(51) Int. Cl.
| A61K 31/714 | (2006.01) |
| A61P 25/28 | (2006.01) |
| A61K 31/197 | (2006.01) |
| A61K 31/375 | (2006.01) |
| A61K 31/4188 | (2006.01) |
| A61K 31/4415 | (2006.01) |
| A61K 31/455 | (2006.01) |
| A61K 31/51 | (2006.01) |
| A61K 31/525 | (2006.01) |

(52) U.S. Cl.
CPC .......... *A61K 31/714* (2013.01); *A61K 31/197* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/525* (2013.01); *A61P 25/28* (2018.01)

(58) Field of Classification Search
CPC ..... A61P 25/28; A61K 31/714; A61K 31/197; A61K 31/375; A61K 31/4188; A61K 31/4415; A61K 31/455; A61K 31/51; A61K 31/525
See application file for complete search history.

(56) References Cited

U.S. PATENT DOCUMENTS

| 5,626,884 A | 5/1997 | Lockett |
| 8,563,609 B2 | 10/2013 | Miller |
| 2003/0008016 A1 | 1/2003 | Crum et al. |
| 2013/0136800 A1* | 5/2013 | Gil Hernandez .. A61K 31/4415 424/602 |
| 2014/0274938 A1 | 9/2014 | Groenendijk et al. |
| 2015/0044138 A1* | 2/2015 | Lansbergen ....... A61K 31/7068 424/9.2 |

FOREIGN PATENT DOCUMENTS

| CN | 102843922 A | 12/2012 |
| CN | 104039318 A | 9/2014 |
| CN | 104256652 A | 1/2015 |
| CN | 104337813 A | 2/2015 |
| CN | 104856048 A | 8/2015 |
| CN | 104922164 A | 9/2015 |
| CN | 102843922 B | 12/2015 |
| EP | 3 308 787 A1 | 4/2018 |
| WO | WO 2003/082339 A1 | 10/2003 |
| WO | WO 2006/108208 A1 | 10/2006 |
| WO | WO 2012/012682 A2 | 1/2012 |
| WO | WO 2015/010449 A1 | 1/2015 |

OTHER PUBLICATIONS

"Analogue" definition obtained from Merriam-Webster Online Dictionary; available at http://www.merriam-webster.com/dictionary/analogue; obtained May 2010. (Year: 2010).*
Cecil Textbook of Medicine, edited by J. Claude Bennett, 20th edition, vol. 2; "Alzheimer's disease and related dementias" by Antonio Damasio, pp. 1892-1896 (Year: 1997).*
"Derivative" definition obtained from Merriam-Webster Online Dictionary; available at http://www.merriam-webster.com/dictionary/derivative; obtained Jul. 2009 (Year: 2009).*
Maczurek, A. et al., Advanced Drug Delivery Reviews, "Lipoic acid as an anti-inflammatory and neuroprotective treatment for Alzheimer's disease", 2008, vol. 60, pp. 1463-1470 (Year: 2008).*
Analog in Saunders Comprehensive Veterinary Dictionary, 3 ed. © 2007 Elsevier, Inc., retrieved from http://medical-dictionary.thefreedictionary.com/analog on Apr. 19, 2016 (Year: 2007).
Demasio, "Alzheimer's disease and related dementias," Cecil Textbook of Medicine, 20(2):1892-1896 (1997).
International Application PCT/CN2017/109280 Written Opinion dated May 31, 2018.
International Application PCT/CN2018/077107 Written Opinion dated Sep. 13, 2018.
Maczurek et al., "lipoic acid as an anti-inflammatory and neuroprotective treatment for Alzheimer's disease," Advanced Drug Delivery Reviews, 2008, vol. 60:1463-1470 (2008).
Malloy, "The Use of Vitamin B Complex and Vitamin C for the Postoperative Patient," J. Natl. Med. Assoc., 42(3):140-146 (1950).
Scheltens et al., "Efficacy of a medical food in mild Alzheimer's disease: A randomized, controlled trial", Alzheimer's & Dementia, 6(1)1-10.e1 (2010).
Scheltens et al., "Efficacy of Souvenaid in Mild Alzheimer's Disease: Results from a Randomized, Controlled Trial". Journal of Alzheimer's Disease, 31(1):225-236 (2012).
Yu et al., "Multi-Vitamin B Supplementation Reverses Hypoxia-Induced Tau Hyperphosphorylation and Improves Memory Function in Adult Mice.", Journal of Alzheimer's Disease, 54(1), 297-306 (2016).

* cited by examiner

*Primary Examiner* — Bahar Craigo
(74) *Attorney, Agent, or Firm* — Jones Day

(57) ABSTRACT

A use of a vitamin composition in preparing a drug for preventing, treating, or delaying Alzheimer's disease. The composition comprises a B vitamins composition or an analog or derivative thereof, vitamin C or an analog or derivative thereof, or a combination of a B vitamins composition or an analog or derivative thereof with vitamin C or an analog or derivative thereof.

7 Claims, 5 Drawing Sheets

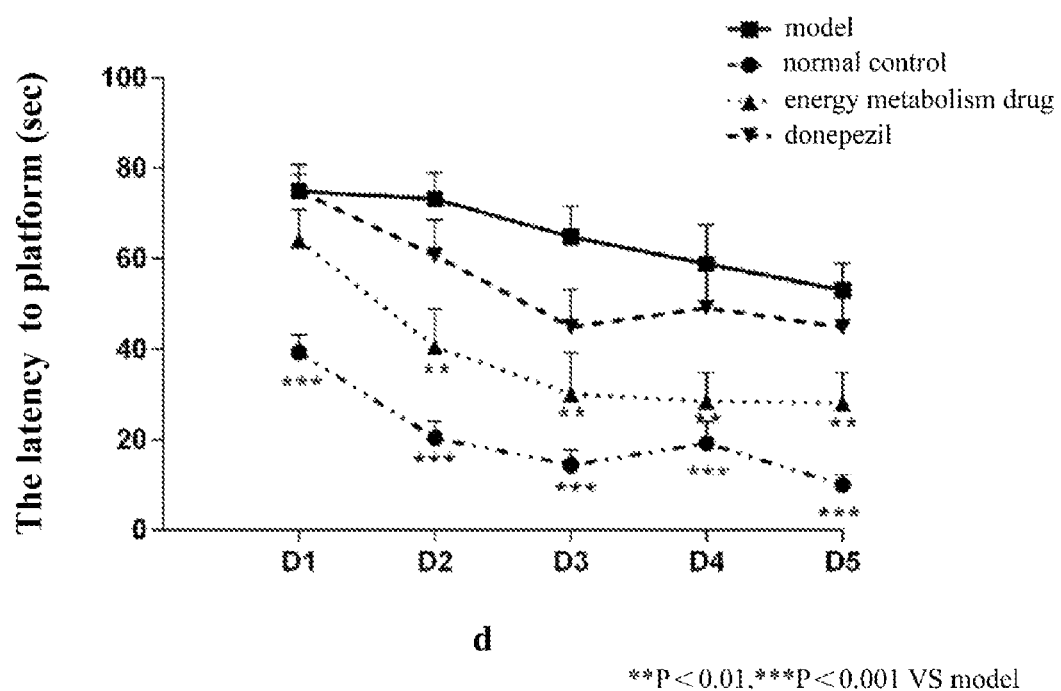
Figure 1. The latency to platform in acquisition test (D1-D5) in each group of animals.

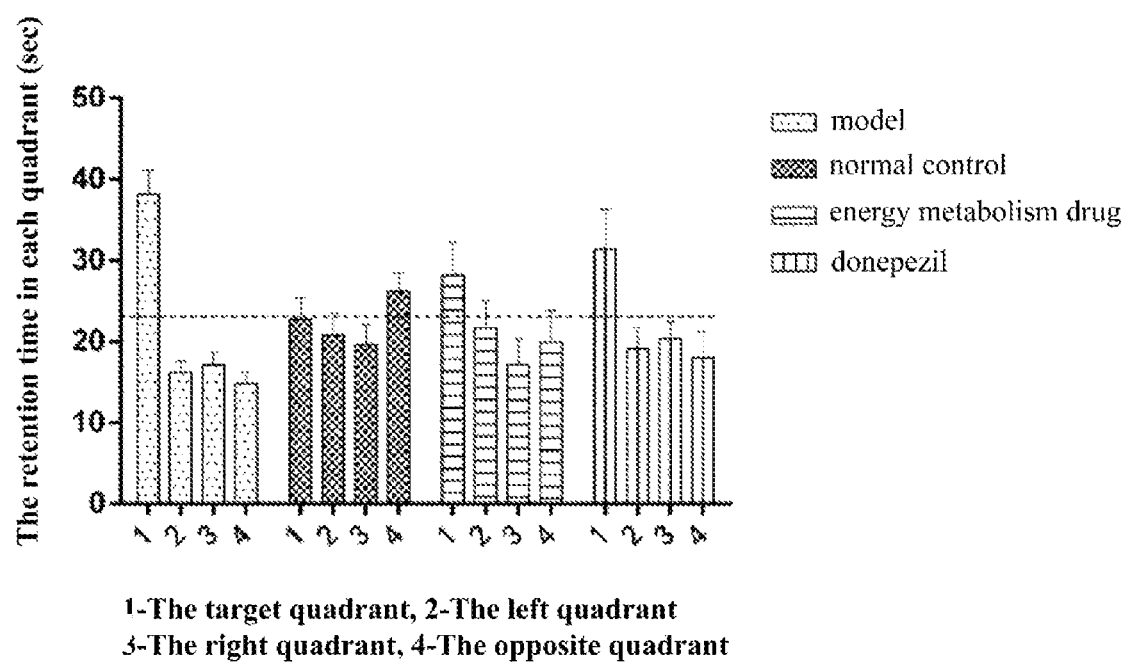
Figure 2: The retention time of each group animals in the target quadrant (1 is the target quadrant).

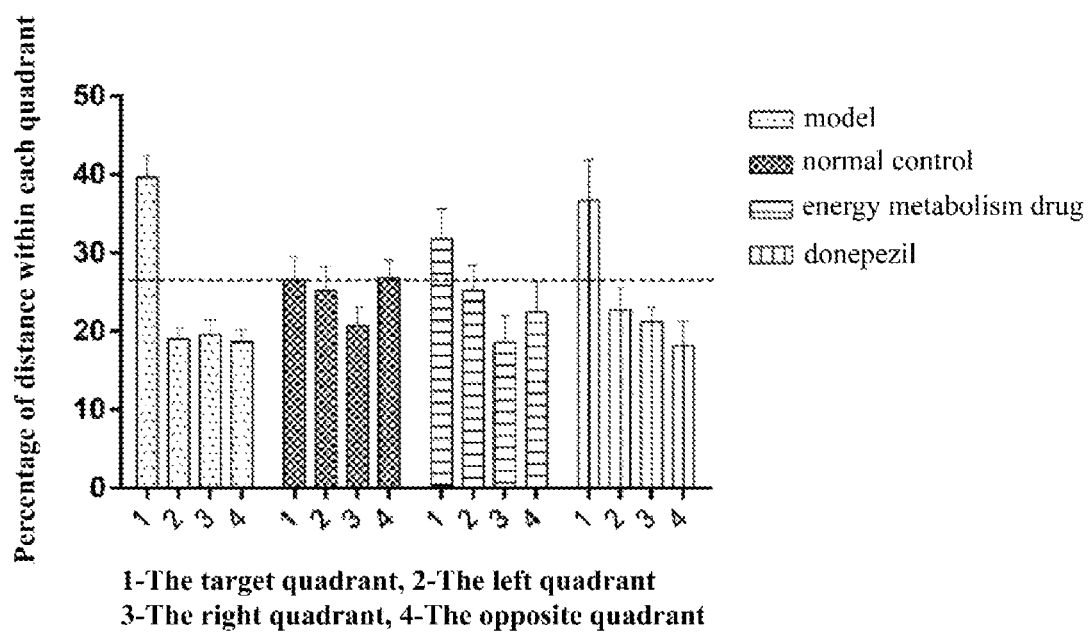
Figure 3: Swimming distance of each group animals in the target quadrant (1 is the target quadrant).

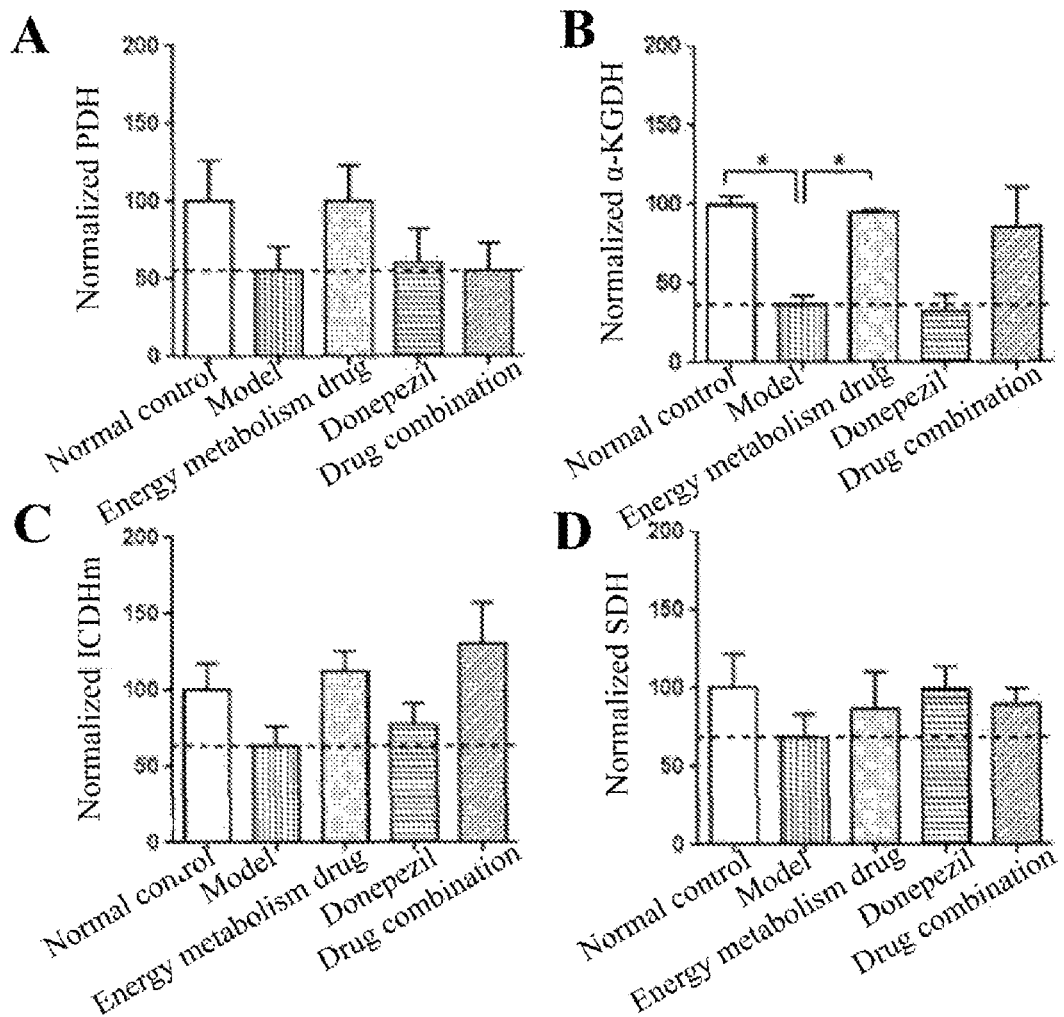
Figure 4: The activity of energy metabolism related enzymes of cerebral cortex.

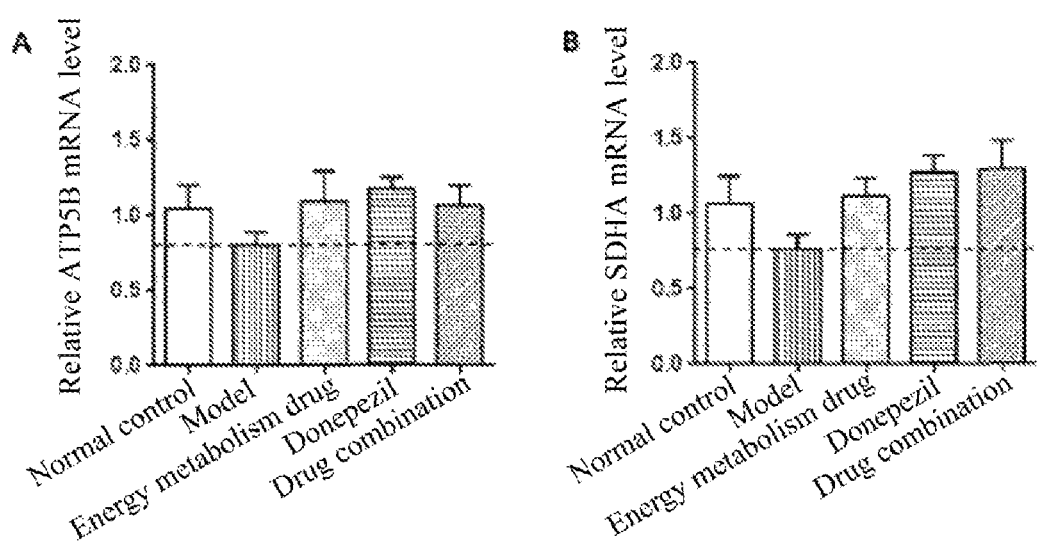
Figure 5: The gene expression of energy metabolism related enzyme of cerebral cortex.

USE OF VITAMIN COMPOSITION IN PREPARING DRUG FOR PREVENTING, TREATING, OR DELAYING ALZHEIMER'S DISEASE

This application is a national stage application of International Patent Application No. PCT/CN2018/077107, filed Feb. 24, 2018, which claims priority to Chinese application No. 201710131111.X, filed Mar. 7, 2017, the disclosures of each of which are hereby incorporated by reference in their entirety.

FIELD OF THE INVENTION

The present invention relates to a vitamins composition, in particular a composition comprising B vitamins composition and C vitamins composition for treatment of Alzheimer's disease by promoting energy metabolism. The present composition is suitable for the prevention, treatment or delaying Alzheimer's disease, the composition can improve learning and memory ability and cognitive impairments.

BACKGROUND OF THE INVENTION

Alzheimer's disease (AD) is a neurodegenerative disease of the central nervous system, usually occurs in people older than 65 years, which is characterized by progressive cognitive decline and behavioral impairment, and is the most common type of senile dementia. At present, the pathogenesis of Alzheimer's disease is not completely clear, metabolic disorders may be one of the reasons of Alzheimer's disease. Sugar is the main source of metabolism in the body, and abnormal glucose metabolism will cause a series of impairment of the tissue functions, in which the brain tissue with glucose as the main energy source is extremely susceptible to abnormal glucose metabolism. Numerous studies have shown that metabolic dysfunction exists in patients with AD, at the same time, cerebral metabolic rate reduction is also one of the earliest symptoms of AD, the changes happen earlier than any function disorders can be detected by neuropsychiatric test. Imageological examination showed that brain atrophy, metabolic disorders and other physiological abnormalities appeared at the same time in patients with AD, and the metabolic abnormalities became worsen with the progression of the disease. It has also been found that the potential mechanism of abnormal glucose metabolism may be related to the direct toxicity of hyperglycemia, insufficient energy supply in the brain caused by hypoglycemia, insulin resistance, insulin signal transduction abnormality and insulin degradation enzyme gene abnormality. It has been confirmed that glucose metabolic rate dropped in frontal and temporal lobe and parietal cingulate cortex can be observed several years before dementia by FDG-PET glucose metabolism imaging, suggesting that the brain glucose metabolism disorder is closely related to the AD, and metabolism disorder is likely to be one reason for the cause and development of AD, therefore it is possible to prevent and reduce the occurrence of AD by improving cerebral energy metabolism.

Glucose glycolysis and the tricarboxylic acid cycle are the main metabolic pathways for glucose production capacity (ATP) in the body. The complete reaction of these two energy metabolism pathways requires the participation of various metabolic enzymes, and the activity of these metabolic enzymes depends on the participation of coenzymes. Pyruvate dehydrogenase is a multi-enzyme complex in the mitochondrial matrix. This enzyme is a key enzyme that catalyzes the oxidative decarboxylation of pyruvate to acetyl-CoA. The reaction process catalyzed by PDH links glycolysis, tricarboxylic acid cycle and ATP formation. Mitochondrial citrate dehydrogenase is the rate-limiting enzyme in the tricarboxylic acid cycle, catalyzing the oxidative decarboxylation of isocitrate to α-ketoglutaric acid. The $H^+$ removed in the catalytic reaction reduces NAD+ to NADH. It is the first step to generate $CO_2$ in the tricarboxylic acid cycle and is also an irreversible reaction, and it is an important rate-limiting step in the Tricarboxylic acid cycle. Alpha-ketoglutarate dehydrogenase (α-KGDH) locating in the mitochondrial matrix is a rate-limiting enzyme involved in the tricarboxylic acid cycle. It is important for maintaining the constant redox of brain tissue, and the activity changer of α-ketoglutarate dehydrogenase is closely related to neurodegenerative diseases. Succinate dehydrogenase is the sixth enzyme in the tricarboxylic acid cycle, which is directly attached to the electron transport chain. Succinate dehydrogenase, flavin adenine dinucleotide, cytochrome and 3 Fe—S proteins are the major components to constitute the mitochondrial complex II, which plays an important role in sugar metabolism and oxidative respiratory chain. SDH exist in the mitochondrial inner membrane and is a marker of the mitochondrial inner membrane. Its activity indicates the metabolic state of tissues and mitochondrial function. SDHA encodes flavoprotein and is a subunit of succinate dehydrogenase. As a key enzyme involved in the tricarboxylic acid cycle, succinate dehydrogenase is one of the marker enzymes that indicates the mitochondrial function, and its activity is generally used as an indicator for evaluating the operation status of the tricarboxylic acid cycle. ATP5B encodes a subunit of ATP synthetase and is involved in hydrogen ion transport in mitochondria. ATP synthetase is a type of synthetase in mitochondria and a key enzyme for energy metabolism in organisms.

Vitamins are a series of essential organic compounds in human metabolism, mainly responsible for maintaining and regulating the body's normal metabolism. They are micronutrients that are needed by living organisms. They are generally not produced by the organisms themselves and need to be obtained by means of diet. Vitamins can't produce energy and make up cells like sugar, protein and fat, but they regulate the metabolism of the organism and maintain the health of the body.

Many vitamins are known to be involved in the metabolism process and they are indispensable elements in the body's biochemical reactions. B vitamins are indispensable substances that promote metabolism in the body and convert sugar, fat, protein, etc. into heat. Most of them participate in the metabolic process in the form of coenzymes. Once vitamin B deficiency occurs in the body, cell function will immediately decrease, causing metabolic disorders. Some of the B vitamin members, such as vitamin B1, are even called psychotropic vitamins because of their good effects on nervous tissue and mental state. B vitamin members including B1, B2, B3, B5, B6, B7 and B12 are directly involved in the glycolysis and tricarboxylic acid cycle during glucose metabolism. Once these vitamins are deficient, this metabolic pathway is bound to cause a series of diseases associated with metabolic disorders. Studies have shown that vitamins B1, B2, B3, B5, B6, B7 and B12 are directly involved in the energy metabolism process. They are also involved in the pathogenesis of AD, such as reducing the production of amyloid (Aβ), promoting the metabolism of homocystein (Hcy), reducing the level of tumor necrosis factor (TNF-α) and assisting the synthesis of neurotransmitters. Therefore, these B vitamin members may affect the occurrence, development and pathological progress of AD by regulating the level of energy metabolism in the brain, and may be one of the potential treatment methods for AD.

In addition to B vitamins, clinical studies have also shown that supplementation with some fat-soluble vitamins such as vitamins D, E and K can reduce the risk of metabolic syndrome, reduce fasting blood glucose levels, induce insulin secretion and increase glucose metabolism in the brain. In addition, they also reduced the levels of Aβ and TNF-α in the brain of AD animals and improved cognitive function in AD patients. It shows that this kind of vitamins can exert their effects both on energy metabolism and nerve function at the same time, and it also suggests that there may be have some relationship between them. Therefore, by taking these vitamins, it is possible to regulate the energy metabolism in the brain of AD patients to improve the symptoms of AD. Microelements are one of the indispensable components in the body, and some microelements have also been reported to participate in energy metabolism and AD progression. Clinical studies have shown that the level of magnesium in the brain of AD patients is significantly lower, and more magnesium intake reduces the risk of AD. Animal studies showed that after 10 min of hypoxia in rats, the ATP level in CA1 area was only 16% of normal, while the ATP level in magnesium ion treated brain slices was 32% of normal brain slices, and magnesium was considered to significantly improve the ATP levels decrease in the CA1 region by hypoxia. Therefore, regulating the level of magnesium in the brain may prevent the deficiency of the energy metabolite ATP in the brain, thereby improving the neurological function in the brain.

Through previous basic researches, vitamins have gradually been confirmed to have benefits in maintaining health and preventing disease. In clinical applications, various vitamins can be used not only as a primary or adjuvant therapy, but also as a dietary supplement to promote health and prevent diseases. Regarding neurological diseases, vitamins such as vitamins B1, B3, B6, B9, B12, C and E can promote neurodevelopment and homocysteine metabolism (high homocysteine is one of the risk factors of AD), regulate neurotransmitter synthesis, prevent neurological disorders caused by pernicious anemia, and improve neurological disorders. They are especially important for maintaining the health of nerve tissue. In clinical applications, these vitamins have significant therapeutic effects on nervous system diseases (dry beriberi), Peripheral neuritis disease, and reducing oxidative stress (a possible pathogenesis of AD).

In terms of energy metabolism, vitamins B1, B2, B3, B5, B7, B6, B9, and B12 are involved in the biological oxidation and the physiological metabolism of carbohydrates, fats, and proteins of the body, thereby promoting energy metabolism and formation. In clinical applications, these vitamins can be used to help treating the symptoms and causes of metabolic-related diseases, such as improving blood sugar regulation and promoting fat metabolism. In view of this, it can be seen that vitamin drugs have extremely high clinical value, and play an extremely important role in the prevention and treatment of energy metabolism diseases, regulation of the nervous system and even delaying the occurrence of AD. Combined with clinical application and basic research results, vitamin drugs are no doubt to have potential value in the treatment of energy metabolism and AD, The study about vitamins for the regulation of energy metabolism in the brain to prevent and reduce the occurrence of AD have social and clinical implications.

Currently, a phase 3 clinical study (NCT00235716) showed that vitamin E for long-term intake (6-48 months) can effectively improve cognitive function in patients with mild cognitive impairment (MCI). Another phase 2 clinical study (NCT01320527) also showed that multivitamins (B9, B12, E and other nutrients) were also beneficial for cognitive and mood regulation in MCI patients, suggesting vitamin treatment in the early stage of cognitive impairment has certain therapeutic effect on AD.

In summary, basic and clinical studies have shown that ① B vitamins (B1, B2, B3, B5, B6, B7 and B12), ② fat-soluble vitamins (D, E, K) and ③ microelement(s) (magnesium ions) all have the effects of regulating metabolism and participating in the protection of neurological function, and early vitamin treatment was also beneficial to the improvement of AD. However, no vitamin drug has been used in clinical to treat AD so far.

At present, the drugs used for the treatment of AD are mainly acetylcholinesterase inhibitors and NMDA receptor antagonists. The above drugs inhibit the decline of cognitive function by changing the levels of neurotransmitters in the brain, but it was known that these drugs can only delay the worsen progression of symptoms by 6-12 months.

The invention prepares a multivitamin drug comprising some or all of the above elements, and aims to improve and prevent AD by regulating and intervening energy metabolism in the brain at an early stage. The energy metabolizing drug of the present invention attempts to improve nerve and cognitive function by improving energy metabolism in the brain from the root, and its mechanism of action is different from the traditional neurotransmitter improvement drugs, and has obvious advantages. Traditional drugs can only cure the symptoms but not the disease. At the same time, the drug disclosed by the invention is relatively safe, and it has no obvious side effects on the body while improving energy metabolism in the brain, and can be regarded as a mild treatment method. Therefore, the energy metabolism drug of the present invention may play an important role in the treatment of AD, providing an innovative drug for the treatment of AD.

Alzheimer's disease has become a global challenge, bringing enormous economic burdens to families and society in the 21st century. According to reports, the economic loss caused by Alzheimer's disease in the United States in 2016 was approximately $236 billion. At present, the drugs used for the treatment of AD are mainly acetylcholinesterase inhibitors and NMDA receptor antagonists. The above drugs inhibit the decline of cognitive function by changing the levels of neurotransmitters in the brain, but it was known that the symptoms worsening could only be delayed by 6-12 months by these drugs. And these drugs can not completely block the progress of AD, which is the biggest problem of AD treatment. The energy metabolism drug involved in the present invention is a novel AD treatment drug. In animal experiments, we found that the drug can effectively improve the cognitive level of the animals, and the mechanism may be related to energy metabolism, which is completely different from the current drug on the market. It is expected that after the drug been approved, the drug would cover a large number of AD patients, and the market prospect will be broad.

DISCLOSURE OF THE INVENTION

A. Summary of the Invention

The present invention relates to a kind of vitamin compositions, particularly, a multivitamin B, C composition for treating Alzheimer's disease by promoting energy metabolism. The composition is suitable for preventing, treating or delaying Alzheimer's disease, improving learning and memory ability, and cognitive dysfunction. The vitamins referred to in this invention comprise their corresponding analogues or derivatives, for example, vitamin B1 means thiamine and analogs or derivatives thereof, vitamin B2 denotes riboflavin and analogs or derivatives thereof; vitamin B3 refers to nicotinic acid and analogs or derivatives thereof; vitamin B5 means pantothenic acid and analogs or derivatives thereof; vitamin B6 means pyridoxine and analogs or derivatives thereof; vitamin B7 is biotin and analogues or derivatives thereof; vitamin B9 means folic acid and analogs or derivatives thereof; vitamin B12 means cyanocobalamine and analogs or derivatives thereof; vitamin C means ascorbic acid and analogs or derivatives thereof; and so on. In one preferred embodiment, the composition comprising B vitamins composition and C vitamins composition is a composition comprising vitamin B1 (thiamine), vitamin B2 (riboflavin), vitamin B3 (nicotinic acid), vitamin B5 (pantothenic acid), vitamin B6, vitamin B7 (biotin), and vitamin C. In one more preferred embodiment, the composition comprising B vitamins composition and C vitamins composition is a composition comprising vitamin B1 (thiamine), vitamin B2 (riboflavin), vitamin B3 (nicotinic acid), vitamin B5 (pantothenic acid), vitamin B6, vitamin B7 (biotin), vitamin B9 (folic acid), vitamin C, choline bitartrate, and inositol. In another more preferred embodiment, the composition comprising B vitamins composition and C vitamins composition is a composition comprising vitamin B1 (thiamine), vitamin B2 (riboflavin), vitamin B3 (niacin), vitamin B5 (pantothenic acid), vitamin B6, vitamin B12, vitamin B7 (biotin), vitamin B9 (folic acid), vitamin C, choline bitartrate, inositol, and p-aminobenzoic acid.

In another aspect, this invention provides a composition comprising an effective amount of a combination of B vitamins composition and C vitamins composition, and a pharmaceutically acceptable carrier. In one preferred embodiment, the composition comprises an effective amount of vitamin B1 (thiamine), vitamin B2 (riboflavin), vitamin B3 (niacin), vitamin B5 (pantothenic acid), vitamin B6, vitamin B7, vitamin C, and a pharmaceutically acceptable carrier. In one more preferred embodiment, the composition comprises an effective amount of vitamin B1 (thiamine), vitamin B2 (riboflavin), vitamin B3 (niacin), vitamin B5 (pantothenic acid), vitamin B6, vitamin B9 (folic acid), vitamin B7 (biotin), vitamin C, choline bitartrate, inositol, and a pharmaceutically acceptable carrier. In another more preferred embodiment, the composition comprises an effective amount of vitamin B1 (thiamine), vitamin B2 (riboflavin), vitamin B3 (niacin), vitamin B5 (pantothenic acid), vitamin B6, vitamin B12, vitamin B9 (folic acid), vitamin B7 (biotin), vitamin C, choline bitartrate, inositol, p-aminobenzoic acid, and a pharmaceutically acceptable carrier.

In yet another aspect, the present invention relates to a composition comprising an effective amount of a combination of B vitamins composition and C vitamins composition, and an effective amount of drug(s) for preventing, treating, or delaying Alzheimer's disease. In one preferred embodiment, the composition comprises an effective amount of vitamin B1 (thiamine), vitamin B2 (riboflavin), vitamin B3 (niacin), vitamin B5 (pantothenic acid), vitamin B6, vitamin B7 (biotin), vitamin C, and an effective amount of drug(s) for preventing, treating, or delaying Alzheimer's disease. In one more preferred embodiment, the composition comprises an effective amount of vitamin B1 (thiamine), vitamin B2 (riboflavin), vitamin B3 (niacin), vitamin B5 (pantothenic acid), vitamin B6, vitamin B9 (folic acid), vitamin B7 (biotin), vitamin C, choline bitartrate, inositol, and an effective amount of drug(s) for preventing, treating, or delaying Alzheimer's disease. In another more preferred embodiment, the composition comprises an effective amount of vitamin B1 (thiamine), vitamin B2 (riboflavin), vitamin B3 (niacin), vitamin B5 (pantothenic acid), vitamin B6, vitamin B12, folic acid, biotin, vitamins C, choline bitartrate, inositol, p-aminobenzoic acid, and an effective amount of drug(s) for preventing, treating, or delaying Alzheimer's disease.

In still yet another aspect, the present invention relates to a composition comprising an effective amount of a combination of B vitamins composition and C vitamins composition, and an effective amount of other vitamin compounds. In one preferred embodiment, the composition comprises an effective amount of vitamin B1 (thiamine), vitamin B2 (riboflavin), vitamin B3 (niacin), vitamin B5 (pantothenic acid), vitamin B6, vitamin B7 (biotin), vitamin C, and an effective amount of other vitamin compounds. In one more preferred embodiment, the composition comprises an effective amount of vitamin B1 (thiamine), vitamin B2 (riboflavin), vitamin B3 (niacin), vitamin B5 (pantothenic acid), vitamin B6, vitamin B9 (folic acid), vitamin B7 (biotin), vitamin C, choline bitartrate, inositol, and an effective amount of other vitamin compounds. In another more preferred embodiment, the composition comprises an effective amount of vitamin B1 (thiamine), vitamin B2 (riboflavin), vitamin B3 (niacin), vitamin B5 (pantothenic acid), vitamin B6, vitamin B12, vitamin B9 (folic acid), vitamin B7 (biotin), vitamin C, choline bitartrate, inositol, p-aminobenzoic acid, and an effective amount of other vitamin compounds. The other vitamin compounds include vitamin A, vitamin D, vitamin E, vitamin K compounds and the like.

In still yet another aspect, the present invention relates to a composition comprising an effective amount of a combination of B vitamins composition and C vitamins composition, and an effective amount of microelement(s). In one preferred embodiment, the composition comprises an effective amount of vitamin B1 (thiamine), vitamin B2 (riboflavin), vitamin B3 (niacin), vitamin B5 (pantothenic acid), vitamin B6, vitamin B7 (biotin), vitamin C, and an effective amount of other vitamin compounds. In one more preferred embodiment, the composition comprises an effective amount of vitamin B1 (thiamine), vitamin B2 (riboflavin), vitamin B3 (niacin), vitamin B5 (pantothenic acid), vitamin B6, vitamin B9 (folic acid), vitamin B7 (biotin), vitamin C, choline bitartrate, inositol, and an effective amount of other vitamin compounds. In another more preferred embodiment, the composition comprises an effective amount of vitamin B1 (thiamine), vitamin B2 (riboflavin), vitamin B3 (niacin), vitamin B5 (pantothenic acid), vitamin B6, vitamin B12, vitamin B9 (folic acid), vitamin B7 (biotin), choline bitartrate, inositol, p-aminobenzoic acid, and an effective amount of other vitamin compounds. The microelements include iron, magnesium, zinc and the like.

The dosage form of the composition comprising B vitamins composition and C vitamins composition of the present invention can be, but not limited to, a chewable tablet; various conventional adjuvants required for preparing different dosage forms can also be added to the composition of the present invention, such as disintegrants, lubricants, binders, antioxidants, complexing agents, and other pharmaceutical carriers to prepare by conventional preparation methods any of the commonly used oral dosage forms, such as dispersible tablets, granules, capsules, oral liquids, and other dosage forms.

The weight ratio of each component for the composition comprising B vitamins composition and C vitamins composition in the present invention can have a plurality of selections, all of which can promote energy metabolism and be used for preventing, treating, or delaying Alzheimer's disease. In certain embodiments, it can include the following components based on weight ratio: 30-300 parts of vitamin B1, 30-300 parts of vitamin B2, 30-300 parts of vitamin B3, 30-300 parts of vitamin B5, 30-300 parts of vitamin B6, 0.01-1 parts of vitamin B7 (biotin), 0.01-2 parts of vitamin B9 (folic acid), 0.01-1 parts of vitamin B12, and 50-500 parts of vitamin C. In one preferred embodiment, the B vitamins composition comprises the following components based on weight ratio: 100 parts of vitamin B1, 100 parts of vitamin B2, 100 parts of vitamin B3, 100 parts of vitamin B5, 100 parts of vitamin B6, 0.1 parts of biotin, 0.4 parts of folic acid, 0.1 parts of vitamin B12, and 150 parts of vitamin C. In one preferred embodiment, the B vitamins composition comprises the following components based on weight ratio: 10 parts of vitamin B1, 15 parts of vitamin B2, 25 parts of vitamin B3, 110 parts of vitamin B5, 10 parts of vitamin B6, 0.1 parts of biotin, and 150 parts of vitamin C. In one more preferred embodiment, the B vitamins composition comprises the following components based on weight ratio: 10 parts of vitamin B1, 15 parts of vitamin B2, 25 parts of vitamin B3, 110 parts of vitamin B5, 10 parts of vitamin B6, 0.1 parts of biotin, 0.4 parts of folic acid, 250 parts of choline bitartrate, 250 parts of inositol, and 150 parts of vitamin C. In one more preferred embodiment, the B vitamins composition comprises the following components based on weight ratio: 10 parts of vitamin B1, 15 parts of vitamin B2, 25 parts of vitamin B3, 110 parts of vitamin B5, 10 parts of vitamin B6, 0.1 parts of biotin, 0.4 parts of folic acid, 250 parts of choline bitartrate, 0.025 parts of vitamin B12, and 150 parts of vitamin C. In another more preferred embodiment, the B vitamins composition comprises the following components based on weight ratio: 10 parts of vitamin B1, 15 parts of vitamin B2, 25 parts of vitamin B3, 110 parts of vitamin B5, 10 parts of vitamin B6, 0.1 parts of biotin, 0.4 parts of folic acid, 250 parts of choline bitartrate, 250 parts of inositol, 0.025 parts of vitamin B12, 50 parts of p-aminobenzoic acid, and 150 parts of vitamin C.

B. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

The term "part," particularly referring to a given quantity, refers to a quantity with a positive or negative deviation within 10%.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein, the term "B vitamins composition" includes all kinds of vitamin B or their corresponding analogues or derivatives, for example, vitamin B1 (thiamine), vitamin B2 (riboflavin), vitamin B3 (nicotinic acid), vitamin B5 (pantothenic acid), vitamin B6 and so on.

As used herein, the terms "analogs" and "analogues" refers to any two or more molecules or fragments that have roughly the same structure and have the same biological activity but can have different levels of activity. The term "derivative" used herein refers to a more complex compound derived from the replacement of a hydrogen atom or group of atoms in a compound by other atoms or groups of atoms.

BRIEF DESCRIPTION OF THE DRAWINGS

FIG. 1: The latency to platform in acquisition test (D1-D5) in each group of animals.
FIG. 2: The retention time of each group animals in the target quadrant (1 is the target quadrant).
FIG. 3: Swimming distance of each group animals in the target quadrant (1 is the target quadrant).
FIG. 4: The activity of energy metabolism related enzymes of cerebral cortex.
FIG. 5: The gene expression of energy metabolism related enzyme of cerebral cortex.

DETAILED DESCRIPTION

Example 1: Therapeutic Effect of Multivitamin on ICV-STZ Indeuced AD Rats

1. Purpose of the Study

The purpose of this study was to evaluate the relationship between Alzheimer's disease and energy metabolism in the brain, and further to evaluate whether vitamin compound can play a role in the prevention and treatment of Alzheimer's disease by regulating energy metabolism in the brain.

2. Experimental Materials 2.1 Reagents
Streptozotocin, vitamin BC tablets (ZENSUN) containing components by weight ratio: 100 parts of vitamin B1, 100 parts of vitamin B2, 100 parts of vitamin B3, 100 parts of vitamin B5, 100 parts of vitamin B6, 0.1 parts of vitamin B7, 0.4 parts of vitamin B9, 0.1 parts of vitamin B12, 150 parts of vitamin C, liquid magnesium, vitamins (D, E, K). Chloral hydrate.
Mitochondrial enzyme activity kit of Solarbio (item number of PDH:MS2103, item number of α-KGDH: MS2100, ICDHm: MS2104, SDH: MS2102), TAKARA SYBR II, total RNA Isolation Kit (TIANGEN), RT-PCR Kit (TOYOBO), Primers (Synthesized by Sangon Biotech).
2.2 Experimental Instruments and Equipment
1. Animal behavior testing equipment: Morris Water Maze of rats
2. Animal behavior video recording and analysis software
3. Rat/Mouse digital brain stereo locator
4. Rat/Mouse Brain stereotactic injection pump
5. Rat/Mouse cranial drill
6. Automated Tissue Homogenization device: Shanghai Jingxin Industrial Development Co., Ltd. JXFSTPRP-24

7. Ultrasonic cell crusher: Ningbo Xinzhi Biological Technology Co., Ltd. JY92-IIDN
8. Thermostatic Water Bath: Shanghai Pingxuan Scientific Instrument Co., Ltd. DK-8D
9. Desk centrifuge: Thermo Scientific FRESCO 17
10. Microplate reader for elisa: Molecular Devices SpectraMax M2
11. PCR instrument: BIORAD CFX-Connect TM Real-Time System Thermal Cycler Block 5020

2.2 Experimental Animals

Male Wistar rat (250-320 g)

3. Experimental Design and Methods 3.1 Intraventricular Injection of Streptozocin in Rats-Preparing the Model of AD (Induced Glucose Metabolism Abnormal in the Brain)

This model was an AD animal model that simulates sporadic AD (SAD) (Icv-STZ model), intracerebral glucose/energy metabolism disorder caused by streptozocin (STZ) injection through the lateral ventricle, successfully mimicked various pathological manifestations of SAD, such as oxidative stress, activation of inflammatory responses, abnormalities in the cholinergic pathway, hyperphosphorylation of tau and aggregation of AB, learning and memory dysfunction. The model needs a short time and there were some cognitive dysfunction and pathological features of AD within a few weeks. It was a relatively quick and easy method to construct AD model, which overcome the time cost of the APPIPS1/tauP301L triple transgenic mouse with AD model. Therefore, this project intends to breed the triple transgenic animal models while building the Icv-STZ model, and verify the effects of vitamins on energy metabolism, prevention and treatment of AD by the same treatment and detection methods. It is expected to repeatedly demonstrate the efficacy of vitamins through different models.

The Icv-STZ model was built as below:

Wistar rats (250-320 g) were anesthetized, fixed on the digital brain stereo locator, depilate the top of the head and disinfect the skin. The median incision at the top of the head was made, exposed the anterior bony, injection was made by microinjector at 0.9 mm behind the bregma, 1.5 mm to the left and right sides of the midline, 3.6 mm vertically from the surface. 5 μL of STZ (3 mg/kg) was slowly inject into the left and right ventricles, the injection time was 8 min, and the needle was left for 2 min, then was slowly withdrawn. All operations are performed under sterile conditions. The skin incision was sterilized with penicillin. Sew up the wound. The sham group received equal volume injection of normal saline.

3.2 Grouping and Administration of Icv-STZ Model Rats

After the Icv-STZ model was established, rats were cultured for one week, and then drug was administered intragastrically for a period of 2 months. Experimental animals were divided into 4 groups: normal control group, model group, treatment group and positive drug group, each group has 20 animals. The specific groups are shown in the table below:

TABLE 1

Icv-STZ model rats groups (n = 20/group)

| Groups | Drug therapy |
| --- | --- |
| Normal control (Icv-saline injection) | vehicle |
| Model (Icv-STZ injection) | vehicle |
| Vitamin (Icv-STZ injection) | multivitamins |
| Positive drug (Icv-STZ injection) | donepezil |

3.3 Verification of Icv-STZ Animal Model

In order to confirm the stability and reliability of the Icv-STZ rat model, at the same time as the formal administration experiment, two other groups as the normal control group (Icy-saline) and the model group (Icv-STZ injection) were set, each group has 20 animals. Behavioral tests were performed 1 month and 2 months after the completion of modeling.

I. Conversion of multivitamin BC tablets to mouse dose= (÷60 kg×12.3 mouse coefficient×5 times dose)

II. Conversion of multivitamin BC tablets to rat dose=(÷60 kg×6.2 rat coefficient×5 times dose)

III. Rats converted to mouse dose=1.98×

Mouse converted to rat dose=0.5×

IV. Animal subcutaneous dose conversion to intragastric administration dose=3×

TABLE 2

Composition of multivitamin BC tablets and dosage

| Component | Rat administration dose mg/kg (Intragastric administration/day) |
| --- | --- |
| Vitamin B1 | 10.28 |
| Vitamin B2 | 10.28 |
| Vitamin B3 | 10.28 |
| Vitamin B5 | 10.28 |
| Vitamin B6 | 10.28 |
| Vitamin B7 | 0.0103 |
| Vitamin B9 | 0.0411 |
| Vitamin B12 | 0.0103 |
| Vitamin C | 15.425 |

3.4 Reagent Preparation a) 0.5% CMC-Na solution: 2.0 g of CMC-Na powder was weighed and 300 ml ultra-pure water was slowly added thereto; the mixture was subjected to magnetic stirring until it was completely dissolved to reach a constant volume of 400 ml, thereby preparing a clear solution of 0.5%, which was stored at 4° C. for later use.

Administration dose of multivitamin BC tablets:

Mouse dose: 1 piece of multivitamin BC tablets÷60 kg×12.3 mouse coefficient×5 times dose=1.025 piece/kg Rat dose: 1 piece of multivitamin BC tablets÷60 kg×6.2 rat coefficient×5 times dose=0.516 piece/kg b) Preparation of multivitamin BC tablets suspension: after grinding of appropriate multivitamin BC tablets, 0.5% CMC-Na was added thereto, and the mixture was subjected to oscillation to become homogeneous, thereby forming a stable suspension. 1.025 piece/kg per mouse and 0.516 piece/kg per rat. Drugs were administered once in the morning and once in the evening.

Dose of positive control drug—donepezil hydrochloride:

Mouse dose: clinical dose (5 mg/d)÷60 kg×12.3 mouse coefficient=1.025 mg/kg

Rat dose: clinical dose (5 mg/d)÷60 kg×6.2 rat coefficient=0.516 mg/kg c) Donepezil hydrochloride solution: Weighted appropriate donepezil hydrochloride powder, 0.5% CMC-Na was added thereto, and the mixture was subjected to oscillation to become homogeneous, thereby forming a stable suspension. Donepezil hydrochloride was administrated as below: 1.025 mg/kg (mouse) and 0.516 mg/kg (rat). The animals were administrated two times one day, donepezil hydrochloride solution in the morning, equal volume 0.5% CMC-Na and multivitamin BC solution in the afternoon.

3.5 Administration Method

Intragastrical administration volume of mouse and rats were 20 mL/kg and 10 mL/kg, respectively. The normal control and the model group were administered with a corresponding volume of 0.5% CMC-Na vitamin BC tablet adjuvant solution by weight.

3.6 Behavioral Tests

Morris Water Maze

The Morris water maze was used as a behavioral tests for studying spatial learning and memory. There were strong escape motivation for rodents in water, they tried to escape from the water environment. The process of learning to escape the water environment reflects the learning ability of animals. Spatially located the safe place (platform) in the water according to the surrounding environment, and swim to the platform purposefully, which could reflect the spatial reference memory ability of the animals. The Morris experimental system consists of a water maze device, an automatic image acquisition and a software analysis system. The Morris water maze unit consists mainly of a pool and a platform with an adjustable height and a movable position.

There were two parts of the water maze experiment:

1) Acquisition Phase

The pool was divided into four quadrants, and the platform was placed in one quadrant with the liquid level over 1 cm of the platform. The animals were placed toward the pool wall into the water, and the position was randomly taken in one of four starting positions in different directions. The time for the animals to find and climb on the platform (escape latency) was recorded to test the animals' learning ability. If an animal has not found the platform for more than 60 s, it needs be guided to the platform. The animals were allowed to stand on the platform for 10 s, then removed, dried under far infrared light and returned to the cage until the next round of experiments. Each animal was trained 4 times a day for 5 days (or longer, depending on the model's learning situation, and the model's average latency <20 s was considered successful).

2) Exploration Training

Exploration training was performed 1.5 hours and 1 day after the acquisition phase. The platform was removed before the experiment, the mice were placed in the water from the opposite side of the original platform quadrant, and started recording 60 s. The spatial memory detection index included: 1) the time of the animal crossed the platform for the first time, 2) the time that the animal spent in the target quadrant (the quadrant where the platform was originally placed); 3) how many times the animal entered into the target quadrant.

3.7 Mitochondrial Enzyme Activity Assay

1) Sampling of Brain Tissue

10% chloral hydrate, deeply anesthetize AD rats, brain tissue was stripped quickly after decapitation the rats. The cerebral cortex was put into a clean and pre-cooled 2 mL centrifuge tube, weight quickly and put into liquid nitrogen for quick freezing, then were collect uniformly, and put in the refrigerator and stored at −80° C.

2) Mitochondrial Enzyme Extraction

The mitochondrial enzyme activity detection kit of Solarbio was used in the experiment. Weighted about 0.1 g cerebral cortex, 1 mL of reagent 1 and 10 µL of reagent 3 were added to the cerebral cortex above, and grinded them with ice bath. The precipitate was removed by centrifugation at 4° C. The supernatant was transferred to another centrifugal tube, the supernatant was removed by centrifugation at 4° C. 200 µL of reagent 2 and 2 µL of reagent 3 were added to the precipitate, ultrasonic disruption, then be used in the enzyme activity detection assay.

3.8 Energy Metabolism Related mRNA Detection

1) Brain Tissue Sampling

10% chloral hydrate, deeply anesthetize AD rats, brain tissue was stripped quickly after decapitation the rats. The cerebral cortex was put into a clean and pre-cooled 2 mL centrifuge tube, weight quickly and put into liquid nitrogen for quick freezing, then were collect uniformly, and put in the refrigerator and stored at −80° C.

2) mRNA Expression

The TIANGEN Total RNA Extraction Kit was used in the experiment. Weighted about 0.1 g cerebral cortex, 1 mL of lysate RZ was added to the cerebral cortex above, then homogenate the sample. Set aside for 5 minutes, 200 µL of chloroform were added to the precipitate, oscillate violently for 15 s, set aside for 3 minutes at room temperature, centrifugation at 4° C. The aqueous phase was moved to a new tube, 0.5 times volume of absolute alcohol was added to the tube and mixed homogeneously. Transferred to CR3 absorption column, the liquid waste was removed by centrifugation at 4° C. Protein removal solution was added, the liquid waste was removed by centrifugation. Rinsed twice with rinsing buffer, the liquid waste was removed by centrifugation. Stored at room temperature for 2 minutes after adding 30-100 µL RNase-Free ddH$_2$O, centrifugated at 4° C. The expression of mRNA was detected by real-time PCR after reverse transcription by TOYOBO RT-PCR Kit.

4 Results

In the acquisition phase of Morris Water Maze (D1-D5), we made the time that the animals take to find the hidden platform as the detection index of spatial memory. The shorter the latency to platform, the better the memory. As showed in FIG. 1, the latency to platform of each group animal shorten significantly as the time of training increasing. It suggested that learning and memory skills improved with repeated training. The learning and memory ability of model animals from D1 to D5 was significantly worse than that of normal control animals. The learning and memory ability of model animals were significantly improved after the treatment of energy metabolize drug (multivitamin BC), indicating that multivitamin BC could significantly improve the learning and memory ability of dementia animals.

In the exploration training, the animals were placed in the water from the opposite side of the original platform quadrant. The time that the animal spent in the target quadrant (the quadrant where the hidden platform was originally placed) and the swimming distances was recorded as the test index of spatial memory. The better the animal's memory ability, the longer time in the target quadrant, and the longer swimming distance. The results were shown in FIG. 2 and FIG. 3. The time and swimming distance of the normal control animals in target quadrant—quadrant 1 (the original hidden platform quadrant) were significantly higher than other group, indicating that their memory level was the best. The time and swimming distance of the Vitamin BC group animals in target quadrant were higher than the model group. It further suggested that VBC therapy for 2 months could effectively improve the memory ability of animals with dementia.

The results of mitochondrial enzyme activity detection assay were shown in FIG. 4. The multivitamin BC significantly improved the activity of key enzymes (pyruvate dehydrogenase (PDH), alpha-ketoglutarate dehydrogenase, mitochondrial isocitrate dehydrogenase (ICDHm), and succinate dehydrogenase (SDH)) involved in the tricarboxylic acid cycle in the cerebral cortex, thus improving mitochondrial metabolism activity.

The results of energy metabolism-related mRNA assay showed that the expressions of SDHA and ATP5B gene in the cerebral cortex of the model animals were lower than those in the normal group, as shown in FIG. 5. The multivitamin BC and combination therapy increased expression of SDHA and ATP5B, improved mitochondrial metabolism, and improve cognitive function.

5 Conclusion

The learning and memory ability of ICV-STZ model rats decreased significantly in the Morris Water Maze experiment. The learning and memory ability of rats improved significantly after multivitamin BC therapy for 2 months. The activity of key enzymes involved in the tricarboxylic acid cycle increased and the expression level of energy metabolism-related mRNA improved in the cerebral cortex. It indicated that this drug has certain therapeutic effect on the treatment for cognitive dysfunction of AD, and it is expected to provide a new class of drugs for AD patients.

In order to describe and understand the present invention more clearly, we describe the present invention by examples in detail. It is clear that modification and alterations of the present invention will be apparent to those skilled in the art without departing from the scope and spirit of the present invention.

What is claimed is:

1. A method for treating or Alzheimer's disease, wherein the method comprises administering a composition to a subject in need thereof, wherein the composition consists of a combination of vitamins, and wherein the combination of vitamins comprises the following components based on weight ratio: 100 parts of vitamin B1, 100 parts of vitamin B2, 100 parts of vitamin B3, 100 parts of vitamin B5, 100 parts of vitamin B6, 0.1 parts of vitamin B7, 0.4 parts of vitamin B9, 0.1 parts of vitamin B12, and 150 parts of vitamin C.

2. The method of claim 1, wherein the composition further comprises an effective amount of other vitamins.

3. The method of claim 2, wherein the other vitamins comprise (i) one or more fat-soluble vitamins, (ii) vitamin A, or (iii) both one or more fat-soluble vitamins and vitamin A.

4. The method of claim 3, wherein the one or more fat-soluble vitamins are selected from the group consisting of vitamin D, vitamin E, and vitamin K.

5. The method of claim 1, wherein the vitamin B1 is thiamine, the vitamin B2 is riboflavin, the vitamin B3 is niacin, the vitamin B5 is pantothenic acid, B7 is biotin, B9 is folic acid, B12 is cyanocobalamine, and the vitamin C is ascorbic acid.

6. The method of claim 1, wherein the composition administered to the subject in need thereof is in an oral dosage form.

7. The method of claim 6, wherein the oral dosage form is chewable tablets, dispersible tablets, granules, capsules, or oral liquids.

* * * * *